United States Patent
Sakuragi (10) Patent No.: US 10,111,713 B2
(45) Date of Patent: Oct. 30, 2018

(54) SURGERY ASSISTANCE APPARATUS, SURGERY ASSISTANCE METHOD AND NON-TRANSITORY COMPUTER-READABLE RECORDING MEDIUM HAVING STORED THEREIN SURGERY ASSISTANCE PROGRAM

(71) Applicant: FUJIFILM Corporation, Tokyo (JP)

(72) Inventor: Futoshi Sakuragi, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 415 days.

(21) Appl. No.: 14/446,572

(22) Filed: Jul. 30, 2014

(65) Prior Publication Data
US 2014/0343586 A1  Nov. 20, 2014

Related U.S. Application Data (63) Continuation of application No. PCT/JP2013/000322, filed on Jan. 23, 2013.

(30) Foreign Application Priority Data

Jan. 31, 2012 (JP) .............................. 2012-018149

(51) Int. Cl.
*A61B 19/00* (2006.01)
*A61B 6/00* (2006.01)
(Continued)

(52) U.S. Cl.
CPC ............ *A61B 19/50* (2013.01); *A61B 5/0033* (2013.01); *A61B 5/7485* (2013.01); *A61B 6/50* (2013.01);
(Continued)

(58) Field of Classification Search
CPC ..... A61B 34/10; A61B 5/0033; A61B 5/7485; A61B 5/4244; A61B 5/1128;
(Continued)

(56) References Cited

U.S. PATENT DOCUMENTS 7,844,320 B2 * 11/2010 Shahidi .................... A61B 5/06
600/407
2002/0147384 A1 * 10/2002 Uchikubo ............ A61B 1/0005
600/109
(Continued)

FOREIGN PATENT DOCUMENTS

JP 2003-33349 A 2/2003
JP 2003-339644 A 12/2003
(Continued)

OTHER PUBLICATIONS

European Office Action in European Application No. 13 743 153. 2-1906 dated May 2, 2016.
(Continued)

*Primary Examiner* — Peter Luong
(74) *Attorney, Agent, or Firm* — McGinn IP Law Group, PLLC (57) ABSTRACT

A medical image obtainment unit that obtains a three-dimensional medical image of a subject to be examined, a target tissue region extraction unit that extracts a region of target tissue from the three-dimensional medical image obtained by the medical image obtainment unit, an abnormal region extraction unit that extracts an abnormal region from the region of target tissue extracted by the target tissue region extraction unit, an excision method obtainment unit that obtains, based on plural excision region determination conditions, plural excision methods in which excision regions satisfying the respective excision region determination conditions are set for the abnormal region, and an excision method presentation unit that presents the plural
(Continued)

excision methods obtained by the excision method obtainment unit are provided.

18 Claims, 6 Drawing Sheets

(51) Int. Cl.
  *G06T 19/00* (2011.01)
  *A61B 17/3205* (2006.01)
  *A61B 6/03* (2006.01)
  *A61B 5/11* (2006.01)
  *A61B 5/00* (2006.01)
  *A61B 34/10* (2016.01)

(52) U.S. Cl.
  CPC ........ *A61B 6/5217* (2013.01); *A61B 17/3205* (2013.01); *A61B 34/10* (2016.02); *G06T 19/00* (2013.01); *A61B 5/1128* (2013.01); *A61B 5/4244* (2013.01); *A61B 6/03* (2013.01); *A61B 2034/104* (2016.02); *A61B 2576/00* (2013.01); *G06T 2207/10072* (2013.01); *G06T 2207/30056* (2013.01); *G06T 2207/30096* (2013.01); *G06T 2207/30101* (2013.01)

(58) Field of Classification Search
  CPC ........... A61B 6/5217; A61B 6/50; A61B 6/03; G06T 2207/30101; G06T 2207/30096; G06T 2207/10072; G06T 2207/30056
  See application file for complete search history.

(56) References Cited

U.S. PATENT DOCUMENTS

| | | | |
|---|---|---|---|
| 2004/0186347 | A1 | 9/2004 | Shose et al. |
| 2006/0020279 | A1* | 1/2006 | Chauhan ................ A61B 90/36 606/167 |
| 2011/0218427 | A1* | 9/2011 | Kitamura .............. G06T 7/0016 600/425 |
| 2012/0032959 | A1 | 2/2012 | Imanaka et al. |
| 2013/0072784 | A1* | 3/2013 | Velusamy .......... A61B 17/3403 600/424 |

FOREIGN PATENT DOCUMENTS

| | | |
|---|---|---|
| JP | 2004-254899 A | 9/2004 |
| JP | 4193201 B2 | 12/2008 |
| WO | WO 2011/118208 A1 | 9/2011 |

OTHER PUBLICATIONS

Extended European Search Report dated May 2, 2016.
International Search Report (ISR) (PCT Form PCT/ISA/210), in PCT/JP2013/000322, dated May 7, 2013.
M. Makuuchi et al., "Surgery for Small Liver Cancers", Seminars in Surgical Oncology, vol. 9, Issue 4, pp. 298-304, 1993.
S. Takahashi et al., "Support System for Hepatectomy Considering Liver Tissue Regeneration after Resection", The Transactions of the Institute of Electronics, Information and Communication Engineers D-II, vol. J80-D-II, No. 5, pp. 1286-1294, 1997.
Extended European Search Report dated Sep. 15, 2015.
Wang Luyao et al: "Implementation of an Interactive Liver Surgery Planning System", Medical Imaging 2011: Visualization, Image-Guided Procedures, and Modeling, SPIE, 1000 20th St. Bellingham WA 98225-6705 USA, vol. 7964, No. 1, Mar. 3, 2011 (Mar. 3, 2011), pp. 1-7, XP060008098 [retrieved on Mar. 1, 2011].
Andrea Schenk, et al. "Clinical Relevance of Model Based Computer-Assisted Diagnosis and Therapy", Proc. SPIE 6915, Medical Imaging 2008: Computer-Aided Diagnosis, vol. 6915, Mar. 17, 2008 (Mar. 17, 2008), pp. 1-19, XP040434900.

* cited by examiner

|  | VOLUME | SURFACE AREA |
|---|---|---|
| EXCISION METHOD 1 (VOLUME) | EVALUATION VALUE a | EVALUATION VALUE c |
| EXCISION METHOD 2 (SURFACE AREA OF CUT SURFACE) | EVALUATION VALUE b | EVALUATION VALUE d |

FIG.10

|  |  | VOLUME | SURFACE AREA |
|---|---|---|---|
| EXCISION REGION 1 | DOMINATED REGION | EVALUATION VALUE e | EVALUATION VALUE g |
| EXCISION REGION 2 | PARTIAL EXCISION REGION | EVALUATION VALUE f | EVALUATION VALUE h |

FIG.11

|  |  |  | VOLUME | SURFACE AREA | DISTANCE |
|---|---|---|---|---|---|
| EXCISION METHOD 1 (VOLUME) | EXCISION REGION 1 | DOMINATED REGION | EVALUATION VALUE e | EVALUATION VALUE g | EVALUATION VALUE i |
|  | EXCISION REGION 2 | PARTIAL EXCISION REGION | EVALUATION VALUE f | EVALUATION VALUE h | EVALUATION VALUE j |
| EXCISION METHOD 2 (SURFACE AREA OF CUT SURFACE) | EXCISION REGION 1 | PARTIAL EXCISION REGION | EVALUATION VALUE k | EVALUATION VALUE m | EVALUATION VALUE i |
|  | EXCISION REGION 2 | DOMINATED REGION | EVALUATION VALUE l | EVALUATION VALUE n | EVALUATION VALUE j |
| EXCISION METHOD 3 (DISTANCE) | EXCISION REGION 1 | DOMINATED REGION | EVALUATION VALUE e | EVALUATION VALUE g | EVALUATION VALUE i |
|  | EXCISION REGION 2 | DOMINATED REGION | EVALUATION VALUE l | EVALUATION VALUE n | EVALUATION VALUE j |

SURGERY ASSISTANCE APPARATUS, SURGERY ASSISTANCE METHOD AND NON-TRANSITORY COMPUTER-READABLE RECORDING MEDIUM HAVING STORED THEREIN SURGERY ASSISTANCE PROGRAM

CROSS-REFERENCE TO RELATED APPLICATIONS

This application is a Continuation of PCT International Application No. PCT/JP2013/000322 filed on Jan. 23, 2013, which claims priority under 35 U.S.C § 119(a) to Japanese Patent Application No. 2012-018149 filed on Jan. 31, 2012. Each of the above applications hereby expressly incorporated by reference, in its entirety, into the present application.

BACKGROUND OF THE INVENTION

Field of the Invention

The present invention relates to a surgery assistance apparatus, method and program that presents an excision region including an abnormal region of an organ, such as a liver and a lung or lungs, in surgery of the organ.

Description of the Related Art

When surgery is performed to excise an abnormal region in an organ, such as a liver and a lung or lungs, a three-dimensional medical image representing the morphology of a target organ is obtained before surgery, for example, by performing CT (Computed Tomography) examination or MRI (Magnetic Resonance Imaging) examination. An excision region is determined in advance based on the three-dimensional medical image.

As a method for determining the excision region based on the three-dimensional medical image, for example, the following method has been proposed. Blood vessels and a bronchus or bronchi are extracted from the three-dimensional medical image, and a region of an organ to which oxygen and nutrition are supplied by a part of these regions that is related to an abnormal region is extracted, as a dominated region. This dominated region is determined, as the excision region.

Meanwhile, a surgical procedure of partial excision has been proposed for surgery of an abnormal region located near the surface of a target organ. The partial excision is performed in such a manner to scoop out a region so as not to damage the blood vessels and the bronchus or bronchi (for example, please refer to M. Makuuchi et al., "Surgery for Small Liver Cancers", Seminars in Surgical Oncology, Vol. 9, Issue 4, pp. 298-304, 1993). Further, Japanese Patent No. 4193201 proposes the following method, as a method for determining an excision region. A region is expanded, based on a diseased region in the liver and plural vessels running through the liver, outward in spherical shape from the center or the center of gravity of the diseased region until the expanded region touches one of the plural vessels. Further, a substantially circular cone region that touches the expanded spherical region is determined as the excision region.

SUMMARY OF THE INVENTION

It is desirable that an excision region is appropriately determined to reduce a burden on a patient due to surgery and the time period of surgery. For example, it is desirable that the surface area of a cut surface of the excision region is as small as possible to reduce a burden on a patient due to surgery and the time period of surgery. It is desirable that the volume of the excision region is as small as possible to keep a normal part of the organ of the patient as much as possible.

From these viewpoints, for example, an excision method may be determined by setting an excision region so as to minimize the surface area of a cut surface of the excision region. Alternatively, an excision method may be determined by setting an excision region so as to minimize the volume of the excision region.

However, if one excision method is determined so as to satisfy one specific condition in this manner, there are cases in which excision is difficult in actual surgery. For example, as in the case in which an abnormal region is present on the back side of a patient, there are cases in which excision is difficult by using the excision method determined as described above, depending on the position of the abnormal region in the target organ or a positional relationship between the target organ and an organ around the target organ.

In view of the foregoing circumstances, it is an object of the present invention to provide a surgery assistance apparatus, method and program that can present a more appropriate excision method that also takes the position of an abnormal region in a target organ and a positional relationship between the target organ and an organ around the target organ into consideration.

A surgery assistance apparatus of the present invention includes a medical image obtainment unit that obtains a three-dimensional medical image of a subject to be examined, a target tissue region extraction unit that extracts a region of target tissue from the three-dimensional medical image obtained by the medical image obtainment unit, an abnormal region extraction unit that extracts an abnormal region from the region of target tissue extracted by the target tissue region extraction unit, an excision method obtainment unit that obtains, based on plural excision region determination conditions, plural excision methods in which excision regions satisfying the respective excision region determination conditions are set for the abnormal region, and an excision method presentation unit that presents the plural excision methods obtained by the excision method obtainment unit.

The surgery assistance apparatus of the present invention may further include a partial excision region extraction unit that sets a smallest enclosing body that encloses the abnormal region extracted by the abnormal region extraction unit, and extracts a region including the set enclosing body and a point on a surface of the target tissue, as a partial excision region, and a dominated region extraction unit that extracts a tubular structure region from the three-dimensional medical image, and extracts a region including a part of the tubular structure region related to the abnormal region and the abnormal region, as a dominated region. Further, the excision method obtainment unit may obtain the excision methods by setting the partial excision region or the dominated region for the abnormal region.

An excision region determination condition for setting the partial excision region or the dominated region may be a distance between the abnormal region and a surface of the target tissue.

One of the plural excision region determination conditions may be the volume of the excision region.

One of the plural excision region determination conditions may be the surface area of a cut surface of the excision region.

The excision method obtainment unit may receive an instruction for correcting the obtained excision methods, and the excision method presentation unit may present the excision methods after correction based on the instruction for correcting.

The excision method obtainment unit may receive an instruction for moving a predetermined excision region in one of the obtained plural excision methods to an excision region in another one of the obtained plural excision methods. Further, the excision method presentation unit may present the excision method after the predetermined excision region has been moved based on the instruction for moving.

The excision method obtainment unit may obtain evaluation values corresponding to the respective excision region determination conditions, and the excision method presentation unit may present the evaluation values obtained by the excision method obtainment unit.

The excision method presentation unit may present a list in which the excision methods corresponding to the respective excision region determination conditions and the evaluation values are correlated with each other.

The medical image obtainment unit may obtain a three-dimensional functional image, as the three-dimensional medical image. Further, the excision method obtainment unit may obtain one of the plural excision methods based on an excision region determination condition that is based on a function level in the three-dimensional functional image.

The target tissue may be a liver, or a lung or lungs.

A surgery assistance method of the present invention includes the steps of obtaining a three-dimensional medical image of a subject to be examined, extracting a region of target tissue from the obtained three-dimensional medical image, extracting an abnormal region from the extracted region of target tissue, obtaining, based on plural excision region determination conditions, plural excision methods in which excision regions satisfying the respective excision region delamination conditions are set for the abnormal region, and presenting the obtained plural excision methods.

A non-transitory computer-readable recording medium having stored therein a surgery assistance program of the present invention stores the program that causes a computer to function as a medical image obtainment unit that obtains a three-dimensional medical image of a subject to be examined, a target tissue region extraction unit that extracts a region of target tissue from the three-dimensional medical image obtained by the medical image obtainment unit, an abnormal region extraction unit that extracts an abnormal region from the region of target tissue extracted by the target tissue region extraction unit, an excision method obtainment unit that obtains, based on plural excision region determination conditions, plural excision methods in which excision regions satisfying the respective excision region determination conditions are set for the abnormal region, and an excision method presentation unit that presents the plural excision methods obtained by the excision method obtainment unit.

According to the surgery assistance apparatus, method and program of the present invention, plural excision methods, in which excision regions satisfying respective excision region determination conditions are set for an abnormal region, are obtained based on the plural excision region determination conditions, and the obtained plural excision methods are presented. Therefore, a doctor can select, from the presented plural excision methods, a more appropriate excision method that also takes the position of the abnormal region in the target organ and a positional relationship between the target organ and an organ around the target organ into consideration.

In the surgery assistance apparatus, method and program of the present invention, when an instruction for correcting the obtained excision methods, as described above, is received, and the excision methods after correction based on the instruction for correcting are further presented, a doctor can select an excision method from a wider variety of choices. Therefore, it is possible to determine a more appropriate excision method.

When an instruction for moving a predetermined excision region in one of the obtained plural excision methods to an excision region in another one of the obtained plural excision methods is received, and the excision method after the predetermined excision region has been moved based on the instruction for moving is presented, it is possible to easily correct the excision method.

When evaluation values corresponding to respective excision region determination conditions are obtained, and the obtained evaluation values are presented, it is possible to present one kind of information to be used by a doctor in judging which excision method is most appropriate. Further, the doctor can judge, with reference to this evaluation value, whether the currently determined excision method should be corrected.

When a three-dimensional functional image is obtained, as the three-dimensional medical image, and one of plural excision methods is obtained based on an excision region determination condition that is based on a function level in the three-dimensional functional image, it is possible to present an excision method that also takes a function level into consideration. Therefore, a doctor can select an excision method from a wider variety of choices. Hence, it is possible to determine a more appropriate excision method.

DESCRIPTION OF THE PREFERRED EMBODIMENTS

Figure 1:
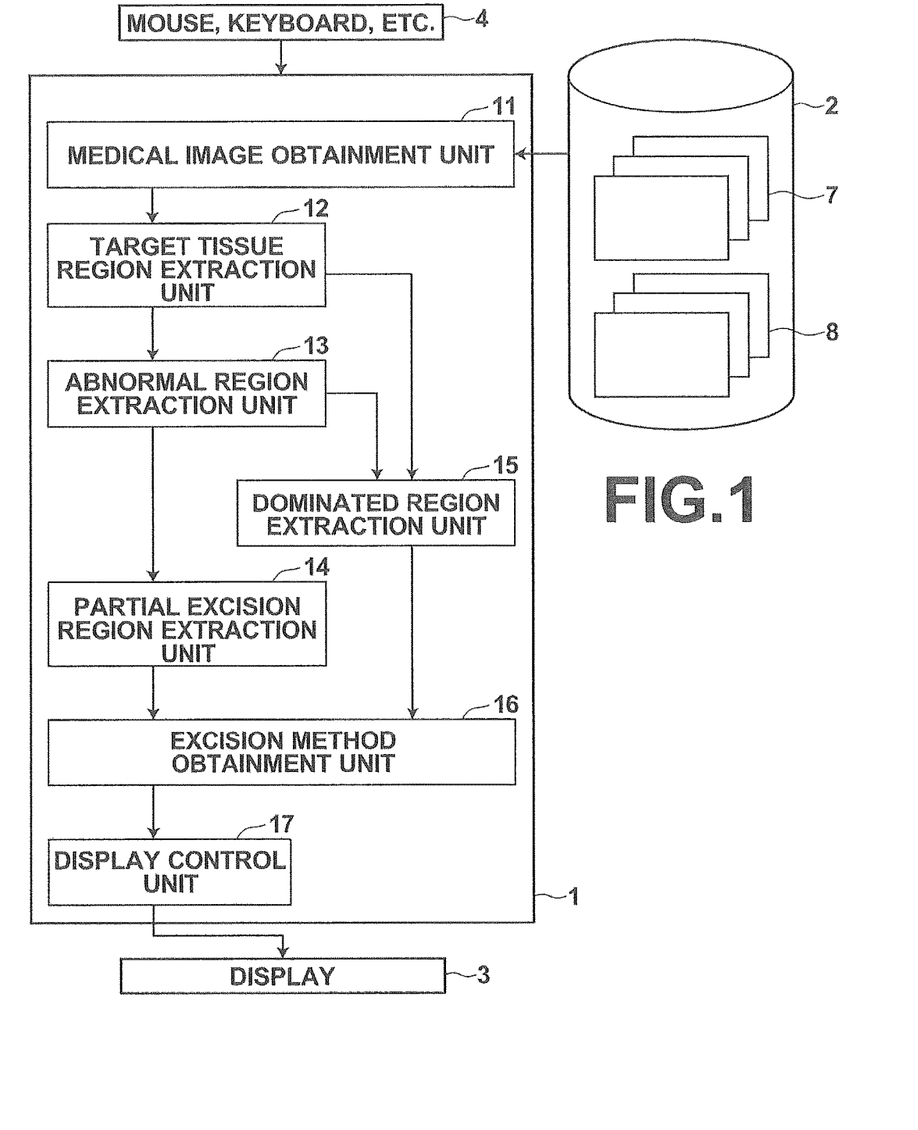
FIG. 1 is a schematic block diagram illustrating the configuration of a surgery assistance system using an embodiment of a surgery assistance apparatus of the present invention.

Hereinafter, an embodiment of a surgery assistance apparatus, a surgery assistance program, and a surgery assistance method of the present invention will be described in detail with reference to drawings. FIG. 1 is a schematic diagram illustrating the configuration of a surgery assistance system including an embodiment of a surgery assistance apparatus according to embodiments of the present invention. As illustrated in FIG. 1, the surgery assistance system according to the embodiment of the present invention includes a surgery assistance apparatus 1, a storage device 2 and a display 3.

The surgery assistance apparatus 1 is a computer in which an embodiment of a surgery assistance program of the present invention has been installed. The computer may be a workstation or a personal computer directly operated by a doctor who makes a diagnosis. Alternatively, the computer may be a server computer connected to them through a network. A surgery assistance program is stored in a recording medium, such as a DVD and a CD-ROM, or in a server computer or the like connected to a network, and which is accessible from the outside. The surgery assistance program is read out, based on a request by a doctor, from the recording medium, the server computer or the like, and downloaded and installed in a computer.

Further, the surgery assistance apparatus 1 includes a central processing unit (CPU), a semiconductor memory, a storage device, such as a hard disk and an SSD (Solid State Drive), in which the aforementioned surgery assistance program has been installed, and the like. This hardware configuration constitutes a medical image obtainment unit 11, a target tissue region extraction unit 12, an abnormal region extraction unit 13, a partial excision region extraction unit 14, a dominated region extraction unit 15, an excision method obtainment unit 16, and a display control unit 17, as illustrated in FIG. 1. When the surgery assistance program installed in the hard disk is executed by the central processing unit, each of the aforementioned units functions. Further, the display 3 and an input device 4, such as a mouse, are connected to the surgery assistance apparatus 1.

The medical image obtainment unit 11 obtains a medical image representing target tissue including a diseased part (abnormal region) to be excised. The medical image obtainment unit 11 according to an embodiment of the present invention obtains a three-dimensional morphological image 7 or a three-dimensional functional image 8, as a medical image. The three-dimensional morphological image 7 is obtained by imaging the liver of a subject to be examined by a CT examination or by an MRI examination. The three-dimensional functional image 8 is obtained by imaging the liver of the subject to be examined by a PET (Positron Emission Tomography) examination or by an SPECT (Single Photon Emission Computed Tomography) examination. Here, the three-dimensional morphological image 7 and the three-dimensional functional image 8 are obtained in advance by imaging, and stored in the storage device 2.

The target tissue region extraction unit 12 receives the three-dimensional morphological image 7 obtained by the medical image obtainment unit 11, and extracts a liver region, which is a region of target tissue, from the three-dimensional morphological image 7. The target tissue region extraction unit 12 according to an embodiment of the present invention calculates a feature value representing the likelihood of the contour of a liver with respect to the value of each voxel data constituting the three-dimensional morphological image 7. Further, the target tissue region extraction unit 12 evaluates the calculated feature value based on an evaluation function obtained in advance by machine learning. Accordingly, the target tissue region extraction unit 12 judges whether the voxel data represent the contour of the liver. The target tissue region extraction unit 12 extracts voxel data representing the contour of the entire liver by repeating this judgment. In the embodiment of the present invention, an AdaBoost algorithm is used to obtain the evaluation function. A liver region may be extracted by using various other known methods. For example, a machine learning method, a statistical analysis method, a linear discriminant method, a neural network, a support vector machine and the like may be used.

The system may be configured in such a manner that the liver region extracted by the target tissue region extraction unit 12 is displayed on the display 3, and that the liver region is correctable by the user using the input device 4.

The abnormal region extraction unit 13 receives the organ region extracted by the target tissue region extraction unit 12, and extracts an abnormal region of the liver, such as an abnormal shadow, from the organ region. As a method for extracting the abnormal region, for example, the three-dimensional morphological image 7 may be displayed on the display. Further, specification of a region by a user using a mouse or the like may be received, and the specified region may be extracted as the abnormal region. Alternatively, the abnormal region may be automatically extracted.

Various known methods may be adopted, as a method for automatically extracting an abnormal region. Specifically, the following methods may be used: methods for detecting a lung cancer disclosed in Japanese Unexamined Patent Publication No. 2003-225231, Japanese Unexamined Patent Publication No. 2003-271924, and "K. Kubota et al., "Evaluation of Computer-Aided Diagnosis system for Lung Cancer based on Helical CT images", The Institute of Electronics, Information and Communication Engineers, Technical Report of IEICE, MI2001-41, pp. 41-46, 2001"; consolidation disclosed in "S. Kido et al., "Intelligent CAD for diffuse lung disease", Grant-in-Aid for Scientific Research granted by the Ministry of Education, Culture, Sports, Science and Technology, Study in Specific Field "Intellectual Diagnosis Aid of Multi-Dimensional Medical Image", Proceedings of 4th Symposium, pp. 45-54, 2007"; Ground-Glass Opacity (GGO); Crazy-Paving; a method for detecting diffuse lung disease, such as honeycomb-shaped shadow, pulmonary emphysema shadow and particle-shaped shadow; a method for detecting a liver cancer disclosed in "Y. Wakida et al., "Liver Cancer Detection based on a Temporal Density Feature from Abdominal Dynamic X-Ray CT Images", Proceedings of Japan Society of Computer-Aided Diagnosis of Medical Images, Vol. 10, No. 1, 2007"; a method for detecting hepatocellular carcinoma, hepatic cyst, hepatic hemangioma, and bleeding in a liver region disclosed in "H. Fujita et al., "Intellectual Computer-Aided Diagnosis Based on Normal Structure Recognition of Human Body", Grant-in-Aid for Scientific Research granted by the Ministry of Education, Culture, Sports, Science and Technology, Study in Specific Field "Intellectual Diagnosis Aid of Multi-Dimensional Medical Image", Proceedings of 4th Symposium, pp. 55-60, 2007", and the like.

The system may be configured in such a manner that the abnormal region that has been automatically extracted by the abnormal region extraction unit 13 is displayed on the display 3, and that the abnormal region is correctable by the user using the input device 4.

Figure 2:
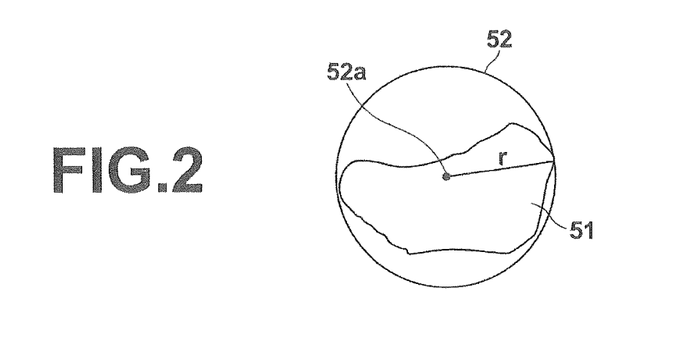
FIG. 2 is a diagram illustrating an example of an enclosing body that is set based on an abnormal region.

The partial excision region extraction unit 14 receives the abnormal region extracted by the abnormal region extraction unit 13, and extracts a partial excision region based on the abnormal region. Specifically, first, the partial excision region extraction unit 14 sets a smallest enclosing body that encloses the abnormal region. FIG. 2 is a diagram illustrating an example of an enclosing body 52 that is set, based on an abnormal region 51, by the partial excision region extraction unit 14. As illustrated in FIG. 2, in the embodiment of the present invention, a circumscribed sphere with a smallest radius enclosing the abnormal region 51 is calculated by using a known method, and the calculated sphere is set as the enclosing body 52. The coordinate of a center 52*a* and radius r of the set enclosing body 52 are stored in a memory.

Figure 3:
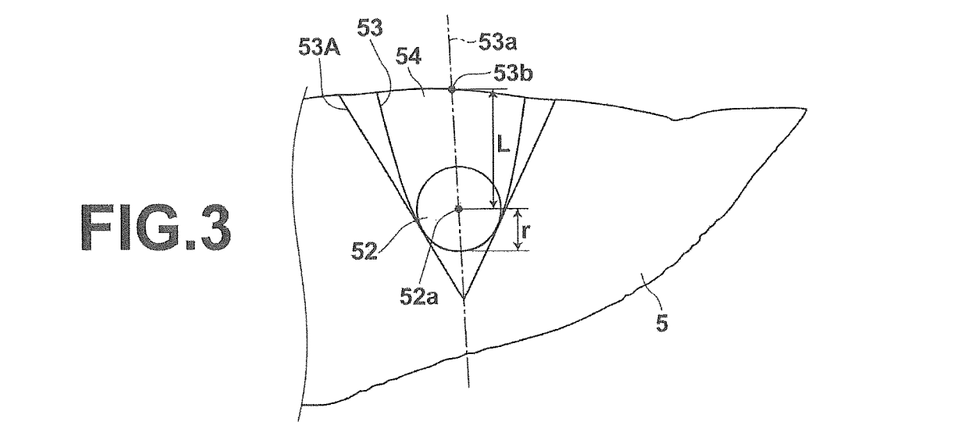
FIG. 3 is a diagram illustrating an example of a partial excision region.

Next, the partial excision region extraction unit 14 extracts, as a partial excision region 54, a region belonging to the inside of a paraboloid of revolution that circumscribes the enclosing body 52. FIG. 3 is a diagram illustrating an example of the partial excision region 54 extracted by the partial excision region extraction unit 14. As illustrated in FIG. 3, in the embodiment of the present invention, a paraboloid 53 of revolution enclosing a sphere, which is the enclosing body 52, is calculated, and a region belonging to the inside of the paraboloid of revolution is extracted as the partial excision region 54.

The partial excision region extraction unit 14 calculates plural paraboloids 53 of revolution circumscribing the enclosing body 52. Further, the partial excision region extraction unit 14 calculates, as partial excision regions 54, a region that belongs to the inside of each of the paraboloids of revolution and has a smallest volume and a region that belongs to the inside of each of the paraboloids of revolution and has a smallest surface area of a cut surface. Here, plural paraboloids of revolution circumscribing the enclosing body 52 are calculated by changing constant a in the following expression (1). Further, the volume and the surface area of a region belonging to the inside of a paraboloid of revolution are calculated for each of the paraboloids of revolution. Then, a region with a smallest volume among the calculated volumes of the regions belonging to the insides of the plural paraboloids 53 of revolution is calculated, as a partial excision region 54. Further, a region with a smallest surface area of a cut surface among the calculated surface areas of cut surfaces of the regions belonging to the insides of the plural paraboloids 53 of revolution is calculated, as a partial excision region 54. Further, data specifying the paraboloids of revolution corresponding to the determined partial excision regions 54, such as an axis 53*a* of a paraboloid of rotation and an intersection 53*b* between the axis 53*a* and the surface of target tissue, are stored in a memory. In the following expression (1), the center 52*a* of a sphere, which is the enclosing body 52, is the origin of the paraboloid of revolution, and the radius of the sphere, which is the enclosing body, is r, and a direction from the center 52*a* of the enclosing body 52, which is the origin, toward the surface of the target tissue is a positive direction of y axis.

[Expression 1]

$$z = a(x^2 + y^2) - r \quad (1)$$

In the embodiment of the present invention, a region belonging to the inside of the paraboloid 53 of revolution circumscribing the enclosing body 52 is determined as the partial excision region 54. However, it is not necessary that the partial excision region 54 is determined in such a manner. For example, a region belonging to the inside of an elliptic paraboloid of revolution circumscribing the enclosing body 52 or a region belonging to the inside of a circular conic surface 53*a* (please refer to FIG. 3) circumscribing the enclosing body 52 may be determined, as the partial excision region.

The system may be configured in such a manner that the partial excision region that has been automatically extracted by the partial excision region extraction unit 14 is displayed on the display 3, and that the partial excision region is correctable by the user using the input device 4.

The dominated region extraction unit 15 receives an organ region extracted by the target tissue region extraction unit 12, and also an abnormal region extracted by the abnormal region extraction unit 13. Further, the dominated region extraction unit 15 extracts a tubular structure region from the organ region, and extracts a region including a part of the tubular structure region related to the abnormal region, as a dominated region.

Figure 4:
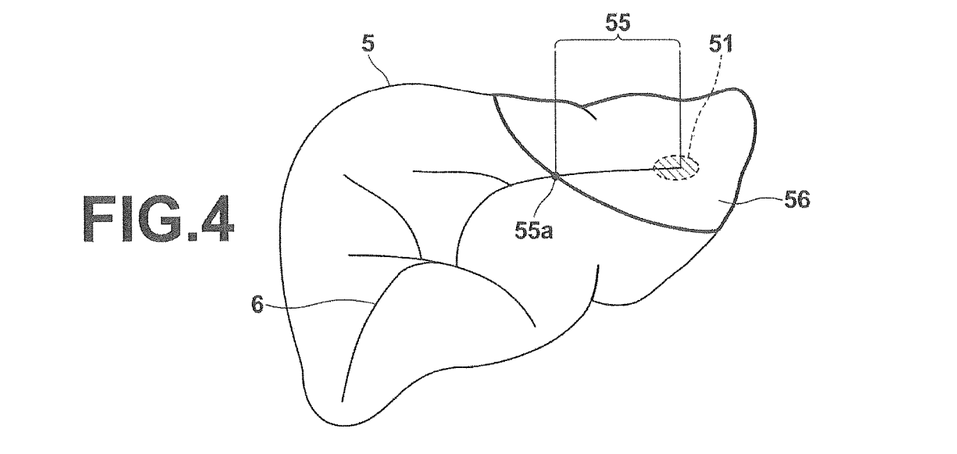
FIG. 4 is a diagram for explaining an example of a method for setting a dominated region.

First, the dominated region extraction unit 15 performs blood vessel region extraction processing and tree structure detection processing on the received liver region 5, as illustrated in FIG. 4. Specifically, a linear structure is probed by calculating eigenvalues of 3×3 Hessian matrix for each local region in the liver region 5. One of the three eigenvalues of the Hessian matrix is close to zero, and the other two eigenvalues are relatively large values in a region including a linear structure. An eigenvector corresponding to the eigenvalue close to zero represents the main axial direction of the linear structure. The dominated region extraction unit 15 utilizes this relationship, and judges the likelihood of a linear structure, based on the eigenvalues of the Hessian matrix, for each local region. Further, when a linear structure is identified in a local region, a center point in the local region is detected as a candidate point.

Further, candidate points detected by probing are connected to each other based on a predetermined algorithm. Accordingly, a tree structure composed of the candidate points and blood vessel branches (edges) connecting the candidate points to each other is constructed. Coordinate information about the plural candidate points that have been detected, and vector information representing the directions of the blood vessel branches are stored in the memory together with identifiers of the candidate points and the blood vessel branches. Then, the contour of a blood vessel (the outer wall of a blood vessel) is identified for each of the detected candidate points in a cross section perpendicular to the path of the blood vessel. The contour of the blood vessel is identified based on the values (CT values) of voxels around each of the detected candidate points. The shape is identified by using a known segmentation method, typified by Graph-Cuts. Through the process as described above, a blood vessel region 6, which is a tubular structure as illustrated in FIG. 4, is extracted, and information that is necessary to identify the extracted blood vessel region 6 is generated, and stored in the memory.

Further, as illustrated in FIG. 4, the dominated region extraction unit 15 extracts a part of the organ including a partial region 55 in the blood vessel region 6 related to the abnormal region and the abnormal region 51, as the dominated region 56. Specifically, first, the dominated region extraction unit 15 sets the partial region 55 in the blood vessel region 6 related to the abnormal region. The partial region 55 may be set by using various known methods. In the embodiment of the present invention, the blood vessel region 6 is displayed on a display, and specification of a position 55a on a blood vessel by an operation of a user at an input device, such as a mouse, is received. Further, a region extending from the received specified position 55a toward the abnormal region is set as the partial region 55. The partial region 55 in the blood vessel region 6 may be set automatically by using a known technique, such as the technique disclosed in Japanese Unexamined Patent Publication No. 2001-283191.

Further, the dominated region extraction unit 15 determines the dominated region 56 based on the partial region 55 in the blood vessel region 6 related to the abnormal region, which is set as described above. As specific methods for determining a dominated region, when the target tissue is, for example, a liver, the following methods may be used to obtain the dominated region. Blood vessels in the liver region are extracted, and blood vessels that dominate regions in the liver region (liver parenchyma or the like) other than the blood vessels are identified by using a Voronoi diagram. Accordingly, regions dominated by respective blood vessels are identified, as liver segments (please refer to Japanese Unexamined Patent Publication No. 2003-033349, "R. Beichel et al., "Liver Segment Approximation in CT Data for Surgical Resection Planning", Medical Imaging 2004: Image Processing, Edited by Fitzpatrick, J. Michael, M. Sonka, Proceedings of the SPIE, Vol. 5370, pp. 1435-1446, 2004", and the like).

Further, when the target tissue is, for example, a lung or lungs, a dominated region may be determined by using the following method. First, a set of voxels in a bronchus region is extracted by using a region growing method, and thinning processing is performed on the extracted bronchus region. Further, voxels on the obtained thin lines representing bronchi are classified, based on the connection relationships between the thin lines, into end points, edges (sides) and branching points. Accordingly, tree structure data representing the bronchi are obtained (for details, please refer to "D. Kobayashi et al., "Trial of Branch Base Tree Structure Model Construction for Blood Vessel Geometric Representation" [on line], RIKEN, RIKEN Symposium on Research on Digitization of Biological Sample's Shape and Construction of its Database, pp. 84-92, 2005, [search conducted on Jan. 6, 2010]", Internet (URL: http://www.comp-bio.riken.jp/keijyo/products/2005 1 files/kobayashi print.pdf), "S. Nakamura et al., "Automated Classification of Pulmonary Artery and Vein from Chest X-Ray CT Images by Tree Structure Analysis", Technical Report of the Institute of Electronics, Information and Communication Engineers, MI, Medical Image, Japan, the Institute of Electronics, Information and Communication Engineers, Vol. 105, No. 580, pp. 105-108, 2006, [search conducted on Nov. 20, 2009]", Internet (please refer to URL: http://www.mura-se.nuie.nagoya-u.ac.jp/~ide/res/paper/J05-ke nkyukai-snaka-1.pdf), and the like). Further, three-dimensional Voronoi division is performed by using the obtained bronchus structure, as a set of seed points. The three-dimensional Voronoi division is performed to find out to which bronchus constituting the bronchus structure each voxel in a lung field region is closest. In other words, the three-dimensional Voronoi division is performed to find out a bronchus that dominates each voxel in the lung field region. Accordingly, a region dominated by the same bronchus is determined as a dominated region of the bronchus (for details, please refer to "Y. Hirano et al., "Quantification of shrinkage of lung lobes in chest CT images using the 3D Voronoi division and application to tumor discrimination" [on line], Proceedings of the 20th Annual Conference of the Japanese Society of Medical Imaging Technology, pp. 315-316, 2001, [search conducted on Nov. 20, 2009]", Internet (URL: http://mase.itc.nagoya-u.ac.jp/~hirano/Papers/JAMIT2001.pd f), and the like). Further, as other examples, Japanese Unexamined Patent Publication No. 2001-137230 and Japanese Unexamined Patent Publication No. 2008-253293 disclose techniques for extracting a lung field. Japanese Unexamined Patent Publication No. 2001-283191 and Japanese Unexamined Patent Publication No. 2002-345807 disclose techniques for extracting a liver. These techniques are applicable.

Various other known methods may be used as long as the method can extract a dominated region.

The system may be configured in such a manner that the blood vessel region 6 and the dominated region 56 that have been automatically extracted by the dominated region extraction unit 15 are displayed on the display 3, and that they are correctable by the user using the input device 4.

The excision method obtainment unit 16 obtains, based on plural excision region determination conditions that have been set in advance, plural excision methods in which excision regions satisfying the respective excision region determination conditions are set for the abnormal region. The excision region determination condition is a condition used when an excision region for each abnormal region is determined. The excision region determination condition is, for example, a condition that the total volume of excision regions that are set for respective abnormal regions is the smallest, a condition that the total surface area of cut surfaces of excision regions that are set for respective abnormal regions is the smallest, and the like.

The excision method obtainment unit 16 obtains one of excision methods by setting excision regions for respective abnormal regions in such a manner to satisfy the aforementioned excision region determination condition.

Specifically, when the excision region determination condition is, for example, a condition that the total volume of excision regions is the smallest, plural excision method candidates are obtained by temporarily setting the aforementioned partial excision regions and dominated regions for respective abnormal regions. Further, the total volume of the excision regions is calculated for each of the excision method candidates. An excision method candidate in which the total volume of the excision regions is the smallest is obtained as an excision method satisfying the excision region determination condition. At this time, a partial excision region having the smallest volume, as described above, may be used as a partial excision region that is temporarily set for an abnormal region.

Further, when the excision region determination condition is, for example, a condition that the total surface area of cut surfaces of excision regions is the smallest, plural excision method candidates are obtained in a similar manner to the aforementioned case by temporarily setting the partial excision regions and dominated regions for respective abnormal regions. Further, the total surface area of cut surfaces of the excision regions is calculated for each of the excision method candidates. An excision method candidate in which the total surface area of cut surfaces of the excision regions is the smallest is obtained as an excision method satisfying the excision region determination condition. At this time, a partial excision region having the smallest surface area of a cut surface, as described above, may be used as a partial excision region that is temporarily set for an abnormal region.

The excision region determination condition is arbitrarily settable by an input by a user using the input device 4. Besides the conditions about the volume and the surface area of a cut surface, as described above, for example, a distance from the surface of the liver to an abnormal region may be used, as the excision region determination condition. When a distance from the surface of the liver to an abnormal region is used as one of excision region determination conditions, one of excision methods may be obtained, for example, by setting the aforementioned partial excision region for an abnormal region if a distance from the surface of the liver to an abnormal region is less than or equal to a predetermined threshold, and by setting the aforementioned dominated region for an abnormal region if a distance from the surface of the liver to the abnormal region is greater than the predetermined threshold. Further, the partial excision region or the dominated region may be set by using conditions about the volume and the radius of the abnormal region together with the condition about the distance.

The distance from the surface of the liver to the abnormal region may be obtained, for example, by calculating a distance between a point on the surface of the liver and the center of gravity of the abnormal region. Further, a point at which the distance between the center of gravity of the abnormal region and the surface of the liver is the shortest may be adopted, as the point on the surface of the liver. Alternatively, a point specified or corrected by an input by a user using the input device 4 may be received, as the point on the surface of the liver.

Further, as one of excision region determination conditions, for example, a condition that the curvature of a cut surface of an excision region is the smallest may be used. Specifically, one of excision methods may be obtained by temporarily setting a partial excision region and a dominated region for an abnormal region, and by calculating the curvatures of cut surfaces of the partial excision region and the dominated region, and by setting an excision region having the smaller curvature for the abnormal region. As a method for calculating the curvature of an excision region, for example, curvatures may be calculated for plural points that are set in the entire excision region, and an average or a median of the plural curvatures may be obtained as the curvature of the excision region. Alternatively, the maximum value of the plural curvatures may be obtained as the curvature of the excision region.

Further, the plural excision methods obtained by the excision method obtainment unit 16 are output to the display control unit 17.

The display control unit 17 makes an image that represents each excision method, obtained by the excision method obtainment unit 16, displayed on the display 3 in such a manner that the image is superimposed on the three-dimensional morphological image 7 of the liver. The image representing the excision method may be generated in such a manner that the excision region is distinguishable from the other region. In the image representing the excision method, an excision region may be, for example, a colored image or a semi-transparent image. Further, the abnormal region 51, the enclosing body 52, the blood vessel region 6, the partial blood vessel region 55, and the like may also be distinguishably displayed on the display 3, for example, by using different colors.

Figure 5:
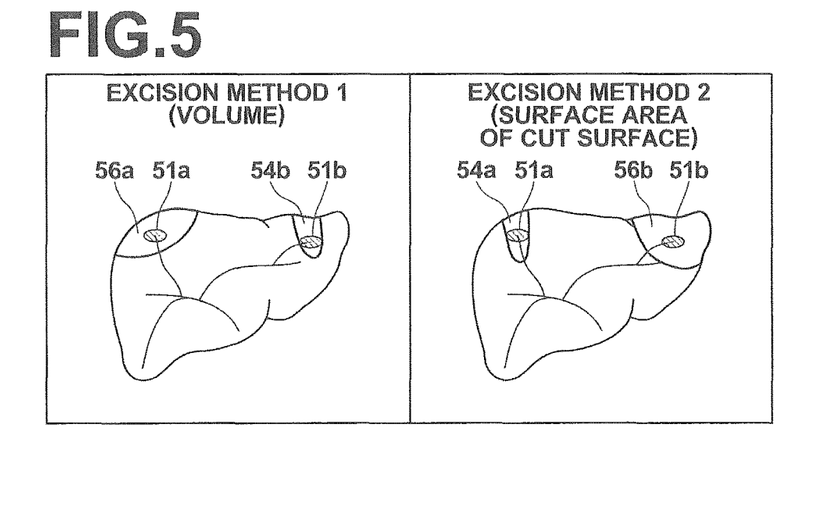
FIG. 5 is a diagram illustrating an example of displaying plural excision methods.

FIG. 5 is a diagram illustrating an example of excision methods displayed on the display 3 by the display control unit 17. FIG. 5 illustrates excision method 1 obtained based on a condition that the total volume of excision regions that are set for respective abnormal regions is the smallest, and excision method 2 obtained based on a condition that the total surface area of cut surfaces of excision regions that are set for respective abnormal regions is the smallest.

Specifically, excision method 1 represents an excision method in which a dominated region, as an excision region, is set for an abnormal region 51a, and a partial excision region, as an excision region, is set for an abnormal region 51b when the excision region determination condition is the condition that the total volume of excision regions is the smallest. Further, excision method 2 represents an excision method in which a partial excision region, as an excision region, is set for the abnormal region 51a, and a dominated region, as an excision region, is set for the abnormal region 51b when the excision region determination condition is the condition that the total surface area of cut surfaces of excision regions is the smallest. FIG. 5 illustrates an example of a mode of displaying plural excision methods. Here, FIG. 5 does not illustrate the accurate volume nor surface area of the excision regions.

FIG. 5 illustrates an example of plural excision methods. The excision methods may be as follows, depending on the position of an abnormal region. For example, a partial excision region, as an excision region, is set for an abnormal region 51a, which is one of abnormal regions, and a dominated region, as an excision region, is set for an abnormal region 51b, which is the other one of abnormal regions. Alternatively, partial excision regions are set for both of the abnormal region 51a and the abnormal region 51b. Alternatively, dominated regions are set for both of the abnormal region 51a and the abnormal region 51b.

The storage device 2 stores, as the three-dimensional anatomical image 7, volume data reconstructed from slice data output from a CT apparatus or an MRI apparatus, volume data output from an MS (Multi Slice) CT apparatus or a cone-beam CT apparatus, or the like.

Further, the storage device 2 stores, as the three-dimensional functional image 8, an SPECT image output from an SPECT apparatus, a functional image generated by analyzing volume data output from an MSCT apparatus, or the like.

Figure 6:
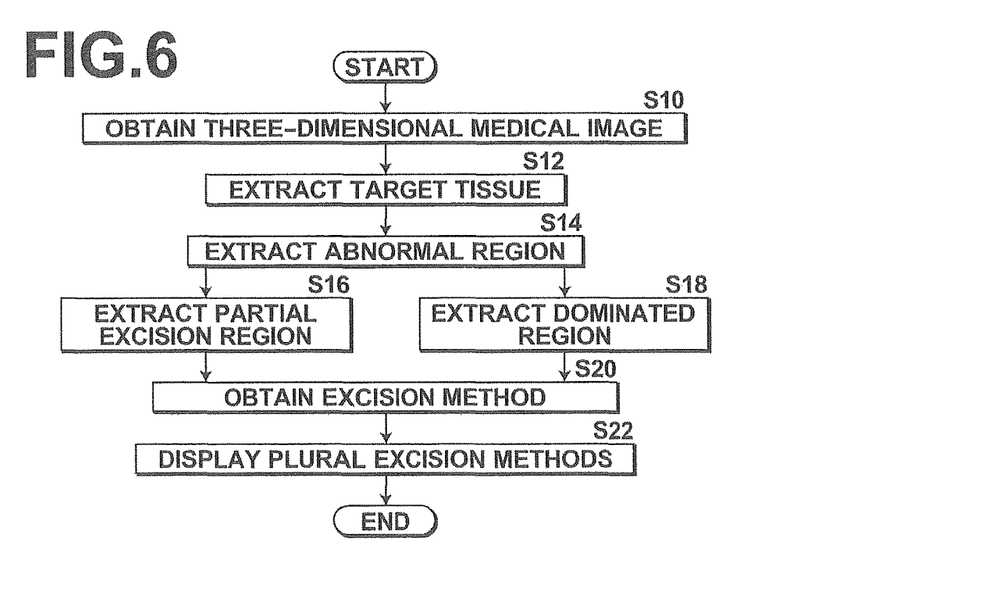
FIG. 6 is a flow chart for explaining an action of the surgery assistance system using an embodiment of the surgery assistance apparatus of the present invention.

FIG. 6 is a flow chart for explaining the action of a surgery assistance system according to an embodiment of the present invention. The action of the surgery assistance system will be described with reference to this flow chart.

In the surgery assistance system according to an embodiment of the present invention, first, a selection menu is displayed on the display 3. When selection of a surgery assistance function according to an embodiment of the present invention at the selection menu is detected, a list of ID's of subjects to be examined is displayed on the display 3. Further, the ID of a subject to be examined who is a surgery target, is selected from the list of ID's of subjects to be examined displayed on the display 3. When the surgery assistance apparatus 1 detects a selection operation by the user, the medical image obtainment unit 11 in the surgery assistance apparatus 1 obtains a medical image or images related to the selected subject to be examined (S10).

Next, the three-dimensional morphological image 7 obtained by the medical image obtainment unit 11 is input to the target tissue region extraction unit 12. The target tissue region extraction unit 12 extracts a liver region from the received three-dimensional morphological image 7 (S12).

Next, the liver region extracted by the target tissue region extraction unit 12 is input to the abnormal region extraction unit 13. The abnormal region extraction unit 13 extracts an abnormal region from the liver region (S14). In the embodiment of the present invention, the three-dimensional morphological image 7 of the liver region is displayed on the display 3, and an abnormal region included in the displayed liver region is specified by a user using the input device 4. The abnormal region extraction unit 13 detects this specification operation by the user, and extracts the detected region, as an abnormal region.

Further, the abnormal region extracted by the abnormal region extraction unit 13 is input to the partial excision region extraction unit 14. The partial excision region extraction unit 14 extracts, based on the received abnormal region, a partial excision region the volume of which is the smallest as described above and a partial excision region in which the surface area of a cut surface is the smallest as described above (S16). Meanwhile, the abnormal region extracted by the abnormal region extraction unit 13 is input also to the dominated region extraction unit 15. The dominated region extraction unit 15 extracts, based on the received abnormal region, dominated regions in parallel to the aforementioned extraction of the partial excision regions (S18).

Then, the partial excision region extracted for each abnormal region by the partial excision region extraction unit 14 and the dominated region extracted for each abnormal region by the dominated region extraction unit 15 are input to the excision method obtainment unit 16.

Then, the excision method obtainment unit 16 obtains, for example based on an excision region determination condition that the total volume of excision regions that are set for respective abnormal regions is the smallest, one of excision methods by setting a partial excision region or a dominated region for each abnormal region so as to satisfy the condition, as described above. Further, the excision method obtainment unit 16 obtains, based on an excision region determination condition that the total surface area of cut surfaces of excision regions that are set for respective abnormal regions is the smallest, one of excision methods by setting a partial excision region or a dominated region for each abnormal region so as to satisfy the condition, as described above (S20).

Figure 7:
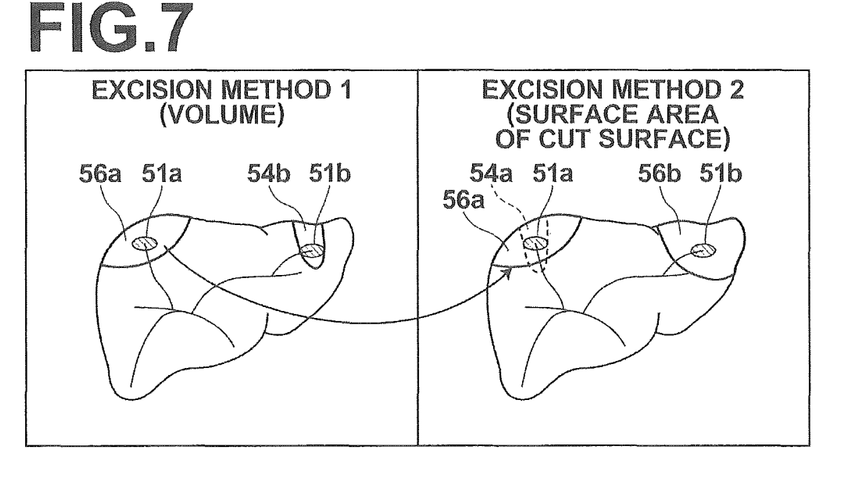
FIG. 7 is a diagram for explaining an example of a method for correcting an excision method.

Further, the plural excision methods obtained by the excision method obtainment unit 16 are output to the display control unit 17. The display control unit 17 makes, based on received plural excision methods, an image displayed on the display 3 by superimposing images representing respective excision methods on the three-dimensional morphological image 7, as illustrated in FIG. 7 (S22).

According to the surgery assistance system in an embodiment of the present invention, plural excision methods in which excision regions satisfying respective excision region determination conditions are set for an abnormal region or regions are obtained based on the plural excision region determination conditions, and the obtained plural excision methods are presented. Therefore, a doctor can select, from the presented plural excision methods, a more appropriate excision method that also takes the position of the abnormal region in the target organ and a positional relationship between the target organ and an organ around the target organ into consideration.

In the aforementioned embodiment, plural excision methods are displayed as a list, as illustrated in FIG. 5. However, the display method is not limited to this method, and excision methods may be displayed in a switchable manner. In this case, for example, an instruction for switching display by a user may be received at the input device 4, and excision methods may be switched based on the instruction for switching.

Further, in the aforementioned embodiments, two excision methods are obtained and displayed, as illustrated in FIG. 5. However, there are cases in which a user wants to further correct the excision methods displayed in this manner, for example, depending on the position of an abnormal region. Therefore, the system may be configured in such a manner that correction is possible by the user using the input device 4, or the like. For example, as illustrated in FIG. 7, when a user wants to change a partial excision region 54a in excision method 2 that has been obtained based on the condition about the surface area of a cut surface of an excision region to a dominated region 56a in excision method 1 that has been obtained based on the condition about the volume of an excision region, the user may select the dominated region 56a by using the input device 4. Further, the user may move the selected dominated region 56a to the position of the partial excision region 54a in excision method 2. Accordingly, it is possible to correct the excision region for the abnormal region 51a to the dominated region. The method for correcting the excision region is not limited to this method, and other methods may be adopted.

Figure 8:
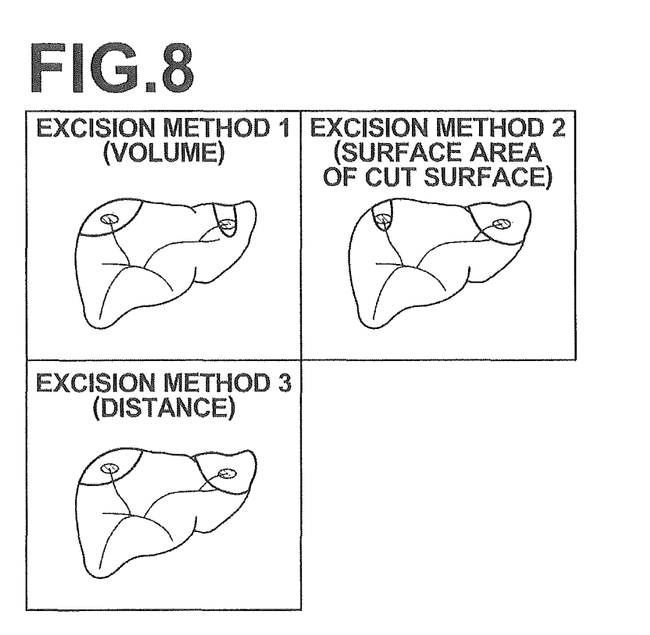
FIG. 8 is a diagram illustrating another example of displaying plural excision methods.

FIG. 5 illustrates an image representing two excision methods. As described above, one of excision methods may be obtained, for example, by using a distance from the surface of the liver to the abnormal region, as an excision region determination condition. Further, an image representing three excision methods may be displayed, as illustrated in FIG. 8.

Figure 9:
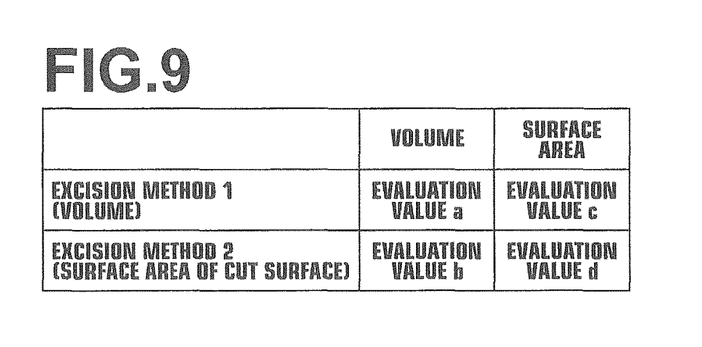
FIG. 9 is a diagram illustrating an example of a list in which excision methods and evaluation values are correlated with each other.

When an image representing plural excision methods, as illustrated in FIG. 5, is displayed, a list of evaluation values corresponding to respective excision methods, as illustrated in FIG. 9, may also be displayed. Here, the term "evaluation value" means a value calculated when each excision region determination condition is judged. The evaluation value is calculated by the excision method obtainment unit 16. For example, as in the aforementioned embodiments, when the total volume of excision regions and the total surface area of cut surfaces of excision regions are used as excision region determination conditions, the display control unit 17 displays the total volume of excision regions in excision method 1 as evaluation value a, the total surface area of cut surfaces of excision regions in excision method 1 as evaluation value c, the total volume of excision regions in excision method 2 as evaluation value b, and the total surface area of cut surfaces of excision regions in excision method 2 as evaluation value d, as illustrated in FIG. 9.

When evaluation values are displayed in this manner, it is possible to present one kind of information to be used by a user in judging which excision method is most appropriate. Further, the user can judge, with reference to this evaluation value, whether the currently determined excision method should be corrected. When the excision method obtained by the excision method obtainment unit 16 is corrected, as described above, it is desirable to update the evaluation value so that the evaluation value corresponding to the corrected excision method is presented.

Figure 10:
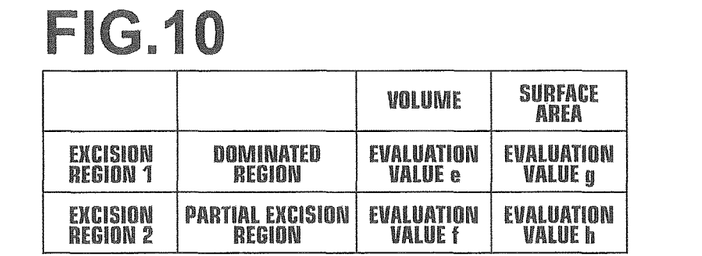
FIG. 10 is a diagram illustrating an example of a list in which excision regions in a predetermined excision method and evaluation values are correlated with each other.

In FIG. 9, the total volume of excision regions for each excision method and the total surface area of cut surfaces of excision regions for each excision method are displayed. Further, excision region types with respect to plural excision regions that are set in each excision method, and evaluation values, such as the volume and the surface area of a cut surface, may be displayed in a list. In FIG. 10, excision region types (a dominated region or a partial excision region) of two excision regions 1, 2 that are set in excision method 1 in FIG. 5 and FIG. 9, the volume and the surface area of a cut surface are displayed as a list. Such an evaluation value for each excision region may be displayed together with the list illustrated in FIG. 9. Alternatively, selection of each excision method illustrated in FIG. 9 may be received, and the evaluation value for each excision region may be displayed based on the selection.

Figure 11:
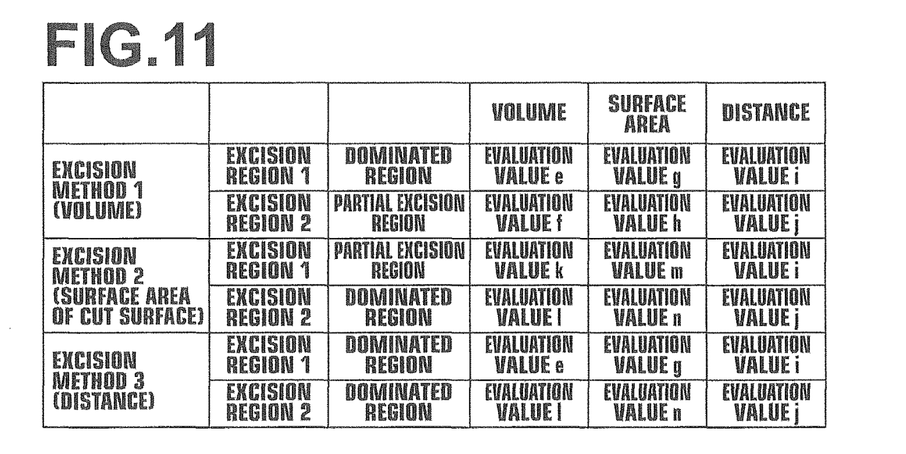
FIG. 11 is a diagram illustrating an example of a list in which excision methods, excision regions in the respective excision methods, and evaluation values are correlated with each other.

Further, as illustrated in FIG. 11, excision region types with respect to plural excision regions that are set in each excision method, and evaluation values, such as volume and the surface area of a cut surface, may be displayed as a list. In FIG. 5, the excision methods are displayed as a three-dimensional morphological image. Alternatively, only the list, as illustrated in FIG. 11, may be displayed.

In the aforementioned embodiment, an excision method is obtained based on an evaluation value, such as volume, surface area and a distance. However, it is not necessary that the excision method is obtained in such a manner. An excision method may be obtained based on a combination of plural evaluation values. For example, an excision method satisfying a condition that the depth of each excision region from the surface of the liver is less than or equal to a predetermined threshold, and a condition that the total volume of respective excision regions is the smallest may be obtained.

Further, in the aforementioned embodiment, an excision method is obtained by using morphological feature values, such as the volume of an excision region, the surface area of a cut surface of the excision region, and a distance from the surface of the liver to an abnormal region, as an excision method determination condition. However, it is not necessary that the excision method is obtained in such a manner. The excision method may be obtained by using functional feature values, as the excision method determination condition.

Specifically, first, the medical image obtainment unit 11 obtains both of the three-dimensional morphological image 7 and the three-dimensional functional image 8. Then, the excision method obtainment unit 16 performs processing for matching positions with each other between the three-dimensional morphological image 7 and the three-dimensional functional image 8. The processing will be described by using the liver, as an example. Positions of the liver region are matched with each other between the three-dimensional morphological image 7 and the three-dimensional functional image 8 by using known rigid or non-rigid registration. Further, a movement direction and a movement amount of each voxel between the images are obtained, and the coordinate values of the liver region extracted from the three-dimensional functional image 8 are transformed by using the movement direction and the movement amount. Consequently, it is possible to make these images at the same coordinate value represent information at the same position of the liver region.

Further, the excision method obtainment unit 16 obtains, for example based on an excision region determination condition that the total function level in excision regions that are set for respective abnormal regions is the highest, one of excision methods by setting a partial excision region or a dominated region for each abnormal region so as to satisfy the condition. Specifically, when a partial excision region and a dominated region are temporarily set for each abnormal region, as excision regions, the partial excision regions or the dominated regions that have the higher total function level in the set excision regions is obtained as final excision regions. Further, the function level may be displayed as an evaluation value together with the excision method also when the excision method is obtained based on the function level in this manner.

Figure 12:
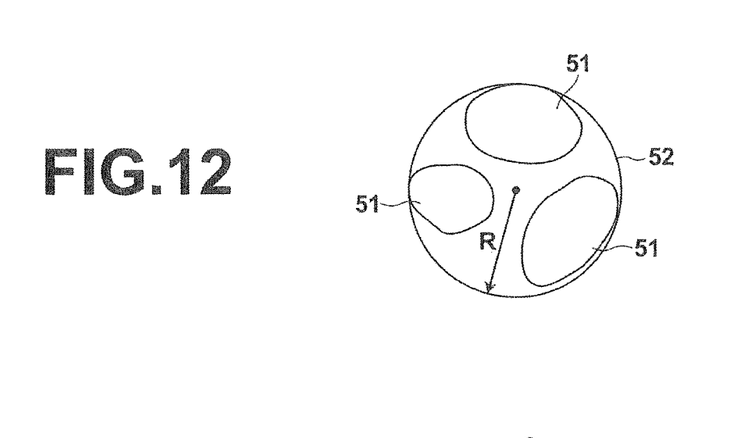
FIG. 12 is a diagram for explaining another method for setting an enclosing body.

Further, in the aforementioned embodiment, a partial excision region is set by setting an enclosing body for an abnormal region. However, it is not necessary that the partial excision region is set in this manner. As illustrated in FIG. 12, when plural abnormal regions 51, as a part of plural abnormal regions 51 extracted by the abnormal region extraction unit 13, are located within predetermined distance R, a smallest enclosing body enclosing all of the plural abnormal regions 51 located within predetermined distance R may be set. When the enclosing body enclosing plural abnormal regions is set in this manner, it is possible to calculate a partial excision region with smaller surface area than the total surface area of cut surfaces of partial excision regions determined for individual abnormal regions 51.

Figure 13:
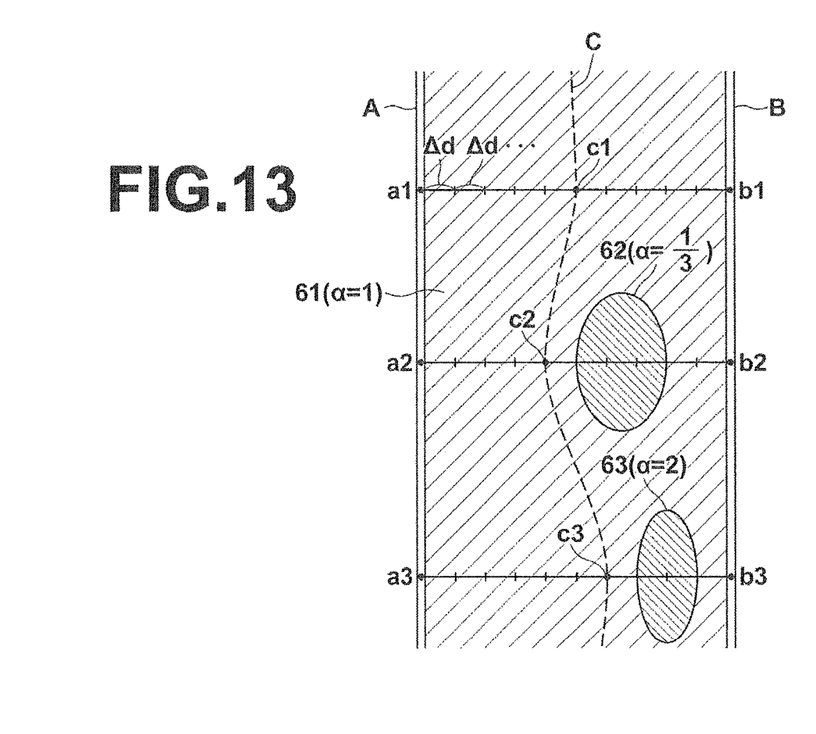
FIG. 13 is a diagram for explaining an example of a method for determining a dominated region based on a three-dimensional functional image.

Further, as a modified example of dominated region extraction processing in the aforementioned embodiment, for example, the medical image obtainment unit 11 may further obtain the three-dimensional functional image 8 representing a function level at each position of the organ. The dominated region extraction unit 15 may extract a dominated region by using the three-dimensional functional image 8. FIG. 13 is a diagram for explaining the modified example of dominated region extraction processing of this example. Here, for the purpose of facilitating understanding, a case in which two blood vessels A, B are parallel to each other and the diameters of the blood vessels A, B are the same is illustrated.

First, the dominated region extraction unit 15 performs processing for matching positions with each other between the three-dimensional morphological image 7 and the three-dimensional functional image 8. This processing for matching positions is performed, as described already.

Next, the dominated region extraction unit 15 determines a region (dominated region) dominated by a blood vessel. Specifically, in each path of point an to point bn (n=1, 2, 3 . . . ) perpendicular to the main axis directions of blood vessels A, B, point cn, which is a boundary between the dominated regions of blood vessels A, B, is obtained by using the following expression (2). Here, α in expression (2) is a function level at each position on the aforementioned path. Plural boundary points obtained by this processing represent boundary line C between the dominated region of blood vessel A and the dominated region of blood vessel B.

[Expression 2]

$$\int_{a_n}^{c_n} \alpha \cdot \Delta d = \int_{b_n}^{c_n} \alpha \cdot \Delta d \qquad (2)$$

In FIG. 13, function level α at each position in region 61 is 1, function level α in region 62 is ⅓, and function level α in region 63 is 2. FIG. 13 illustrates a specific example of boundary points cn determined on three paths of point an to point bn (n=1, 2, 3), on which the distributions of function level at each position are different from each other. As illustrated in FIG. 13, a distance from the center line of a blood vessel to the boundary of the dominated region of the blood vessel depends on the distribution of function level on the path. Specifically, the distance from the center line of each blood vessel to the boundary of its dominated region is longer as function level α on the path is lower, and the distance is shorter as function level α on the path is higher.

When the dominated region is set based on the function level of an organ in this manner, it is possible to automatically set a more appropriate excision region when the dominated region is determined as the excision region.

In the aforementioned embodiment, the volume of a non-excision region, excluding the excision region, may be calculated for each excision method, and when the volume of the non-excision region reaches ⅓ of the volume of the entire liver, an alert may be issued. Generally, it is desirable that the volume of the remaining part of the liver after excision is at least ⅓ of the volume of the entire liver. Therefore, it is possible to provide a guide for setting the volume of the excision region within an appropriate range. Accordingly, it is possible to assist the user in appropriately setting the excision region.

In each of the embodiments, the surgery assistance apparatus 1 is realized by installing each program in a computer. Alternatively, programs may be installed in plural computers in a distributed manner to configure a surgery assistance system that has a function similar to the surgery assistance apparatus 1.

In the aforementioned embodiment, a case of outputting plural excision methods and the like by the surgery assistance apparatus 1 by means of display was described. However, the output method is not limited to this method. For example, a print may be output, or data may be output (recording on a medium, such as a CD-R and DVD, or transferring data through a network).

The aforementioned embodiments illustrate a case in which the target tissue is a liver and a tubular structure for determining a dominated region is a blood vessel. However, the target tissue of the present invention is not limited to the liver. The present invention is applicable to assistance in surgery of other organs, such as a lung.

What is claimed is:

1. A surgery assistance apparatus that is connected to a display device, the apparatus comprising:
    a memory; and
    a processor connected to the memory and configured to:
        obtain a three-dimensional medical image of a subject to be examined;
        extract a region of target tissue from the obtained three-dimensional medical image;
        extract an abnormal region from the extracted region of target tissue;
        obtain, based on each of at least two excision region determination conditions, at least two excision methods, each of which is classified by excision regions satisfying the each of at least two excision region determination conditions for the abnormal region; and
        display images on the display device, of the at least two obtained excision methods,
    wherein each of the images is generated according to each of the at least two excision methods, and is displayed on the display device so that an excision region which is determined by each of the at least two excision methods, is distinguishable from another region,
    wherein the processor obtains evaluation values corresponding to the respective excision region determination conditions,
    wherein the display device displays the obtained evaluation values, and
    wherein the display device displays a list in which the excision methods corresponding to the respective excision region determination conditions and the evaluation values are correlated with each other.

2. The surgery assistance apparatus, as defined in claim 1, wherein the processor is further configured to:
    set a smallest enclosing body that encloses the extracted abnormal region, and extract a region including the set enclosing body and a point on a surface of the target tissue, as a partial excision region; and
    extract a tubular structure region from the three-dimensional medical image, and a region including a part of the tubular structure region related to the abnormal region and the abnormal region, as a dominated region,
    wherein the processor obtains the excision methods by setting the partial excision region or the dominated region for the abnormal region.

3. The surgery assistance apparatus, as defined in claim 2, wherein an excision region determination condition for setting the partial excision region or the dominated region is a distance between the abnormal region and a surface of the target tissue.

4. The surgery assistance apparatus, as defined in claim 1, wherein one of the at least two excision region determination conditions is the volume of the excision region.

5. The surgery assistance apparatus, as defined in claim 1, wherein one of the at least two excision region determination conditions is the surface area of a cut surface of the excision region.

6. The surgery assistance apparatus, as defined in claim 1, wherein the processor receives an instruction for correcting the obtained excision methods, and
    wherein the display device displays the excision methods after correction based on the instruction for correcting.

7. The surgery assistance apparatus, as defined in claim 6, wherein the processor receives an instruction for moving a predetermined excision region in one of the obtained excision methods to an excision region in another one of the obtained excision methods, and wherein the display device displays the excision method after the predetermined excision region has been moved based on the instruction for moving.

8. The surgery assistance apparatus, as defined in claim 1, wherein the processor obtains a three-dimensional functional image, as the three-dimensional medical image, and
    wherein the processor obtains one of the at least two excision methods based on an excision region determination condition that is based on a function level in the three-dimensional functional image.

9. The surgery assistance apparatus, as defined in claim 1, wherein the target tissue is a liver.

10. The surgery assistance apparatus, as defined in claim 1, wherein the target tissue is a lung or lungs.

11. The surgery assistance apparatus, as defined in claim 1, wherein the at least two excision region determination conditions are set in advance of the processor obtaining the at least two excision methods.

12. The surgery assistance apparatus, as defined in claim 1, wherein the excision region determination condition comprises a condition used when an excision region for each abnormal region is determined.

13. The surgery assistance apparatus, as defined in claim 1, wherein the excision region determination condition comprises at least two of:
    a condition that the total volume of excision regions that are set for respective abnormal regions is the smallest among a total volume of excision regions of excision method candidates;
    a condition that the total surface area of cut surfaces of excision regions that are set for respective abnormal regions is the smallest among a total surface area of cut surfaces of excision regions of excision method candidates; or
    a condition that a curvature of a cut surface of an excision region is the smallest among curvatures of cut surfaces of excision regions of excision method candidates.

14. The surgery assistance apparatus, as defined in claim 13, wherein the excision region determination condition comprises a condition that the total volume of excision regions is the smallest total volume among a total volume of excision regions of excision method candidates, and wherein the processor:
obtains the excision method candidates by temporarily setting partial excision regions and dominated regions for respective abnormal regions;
calculates a total volume of the excision regions for each of the excision method candidates; and
obtains an excision method candidate in which a total volume of the excision regions is the smallest total volume, as an excision method satisfying the excision region determination condition.

15. The surgery assistance apparatus, as defined in claim 13, wherein the excision region determination condition comprises a condition that the total surface area of cut surfaces of excision regions is the smallest among a total surface area of cut surfaces of excision regions of excision method candidates, and wherein the processor:
obtains a plurality of excision method candidates by temporarily setting partial excision regions and dominated regions for respective abnormal regions;
calculates a total surface area of cut surfaces of the excision regions for each of the excision method candidates; and
obtains an excision method candidate in which a total surface area of cut surfaces of the excision regions is the smallest total surface area, as an excision method satisfying the excision region determination condition.

16. The surgery assistance apparatus, as defined in claim 1, wherein the images of the at least two obtained excision methods comprises:
a first image depicting the target tissue according to a first excision method of the at least two obtained excision methods; and
a second image of the target tissue according to a second excision method of the at least two obtained excision methods, and
wherein the first and second images are displayed side-by-side on the display device.

17. A surgery assistance method comprising the steps of:
obtaining a three-dimensional medical image of a subject to be examined;
extracting a region of target tissue from the obtained three-dimensional medical image;
extracting an abnormal region from the extracted region of target tissue;
obtaining, based on each of at least two excision region determination conditions, at least two excision methods, each of which is classified by excision regions satisfying the each of at least two excision region determination conditions for the abnormal region; and
displaying on a display device, images of the at least two obtained excision methods,
wherein each of the images is generated according to each of the at least two methods, and is displayed on the display device so that an excision region which is determined by each of the at least two excision methods, is distinguishable from another region,
wherein the method further comprises:
obtaining evaluation values corresponding to the respective excision region determination conditions,
wherein the display device displays the obtained evaluation values, and
wherein the display device displays a list in which the excision methods corresponding to the respective excision region determination conditions and the evaluation values are correlated with each other.

18. A non-transitory computer-readable recording medium having stored therein a surgery assistance program that is executable by a computer to cause the computer to:
obtain a three-dimensional medical image of a subject to be examined;
extract a region of target tissue from the obtained three-dimensional medical image;
extract an abnormal region from the extracted region of target tissue;
obtain, based on each of at least two excision region determination conditions, at least two excision methods, each of which is classified by excision regions satisfying the each of at least two excision region determination conditions for the abnormal region; and
display on a display device, images of the at least two obtained excision methods,
wherein each of the images is generated according to each of the at least two excision methods, and is displayed on the display device so that an excision region which is determined by each of the at least two excision methods, is distinguishable from another region,
wherein the surgery assistance program is further executable by the computer to cause the computer to:
obtain evaluation values corresponding to the respective excision region determination conditions,
wherein the display device displays the obtained evaluation values, and
wherein the display device displays a list in which the excision methods corresponding to the respective excision region determination conditions and the evaluation values are correlated with each other.

* * * * *